United States Patent [19]
Furumoto

[11] Patent Number: 5,066,293
[45] Date of Patent: *Nov. 19, 1991

[54] LIGHT AMPLIFIER AND METHOD OF PHOTOTHEMOLYSIS

[75] Inventor: Horace Furumoto, Wellesley, Mass.

[73] Assignee: Candela Laser Corporation, Wayland, Mass.

[*] Notice: The portion of the term of this patent subsequent to May 9, 2006 has been disclaimed.

[21] Appl. No.: 322,618

[22] Filed: Mar. 10, 1989

Related U.S. Application Data

[63] Continuation of Ser. No. 939,262, Dec. 8, 1986, Pat. No. 4,829,262, which is a continuation of Ser. No. 664,525, Oct. 25, 1984, abandoned.

[51] Int. Cl.⁵ .............................................. A61N 5/06
[52] U.S. Cl. ......................................... 606/9; 606/17; 128/396; 128/898; 359/346
[58] Field of Search ...................... 128/302.1, 362, 395, 128/355, 397, 398; 372/25, 31, 53, 99, 93, 95; 330/4.3; 606/9–13, 16–19

[56] References Cited

U.S. PATENT DOCUMENTS

| | | | |
|---|---|---|---|
| 3,315,680 | 4/1967 | Silbertrust et al. | 606/4 |
| 3,793,541 | 2/1974 | Ashkin et al. | |
| 3,805,187 | 4/1974 | Lempicki et al. | |
| 4,013,978 | 3/1977 | Burlamacchi et al. | |
| 4,267,524 | 5/1981 | Paxton et al. | |
| 4,829,262 | 5/1989 | Furamoto | 128/355 |

OTHER PUBLICATIONS

R. Rox Anderson et al., "Selective Photothermolysis: Precise Microsurgery by Selective Absorption of Pulsed Radiation", *Science*, Apr. 29, 1983, vol. 220, pp. 524–527.

F. N. Baltakov et al., "110-J Pulsed Laser Using a Solution of Rhodamine 6G in Ethyl Alcohol", *Soviet Physics-Technical Physics*, vol. 17, No. 7, Jan. 1973, pp. 1161–1163.

P. Burlamacchi et al., "Self-Guiding Flashlamp-Pumped Dye Lasers", *Applied Optics*, Jan. 1975, vol. 14, No. 1, pp. 79–93.

Jeffrey Greenwald et al., "Comparative Histological Studies of the Tunable Dye (at 577 nm) Laser and Argon Laser: The Specific Vascular Effects of the Dye Laser", *The Journal of Investigative Dermatology*, vol. 77, No. 3, 1981, pp. 305–310.

J. B. Marling et al., "Long-Pulse Dye-Laser Emmission Across the Visible Spectrum", Abstract, *IEEE Journal of Quantum Electronics*, Oct. 1971, pp. 198–199.

J. B. Marling et al., "Laser Characteristics of Seventeen Visible-Wavelength Dyes Using a Coaxial-Flashlamp-Pumped Laser", *Applied Optics*, Oct. 1974, vol. 13, No. 10, pp. 2317–2320.

R. Pappalardo et al., "Long Pulse Laser Emission From Rhodamine 6 G Using Cyclooctatetraene", *Applied Physics Letters*, vol. 16, No. 7, Apr. 1, 1970, pp. 267–268.

Romano Pappalardo et al., "Long-Pulse Laser Emission From Rhodamine 6G".

V. S. Smirnov, "Methods for Reducing the Divergence of Lamp-Excited Rhodamine 6G Solution Lasers", Opt. Spectrosc. (USSR), 49(5), Nov. 1980, ©1981, *The Optical Society of America*, pp. 526–529.

Primary Examiner—David Shay
Attorney, Agent, or Firm—Hamilton, Brook, Smith & Reynolds

[57] ABSTRACT

A tunable dye laser has been found particularly suited to selective photothermolysis. A longer pulse duration which makes the system suitable for a wider range of applications is obtained by modifying the laser to generate a spatially noncoherent beam. The optical system at each end of the laser cell, which may include a lens or spherical mirror, refocuses the aperture of the dye cell near to itself so that substantially all light emanating from the dye cell is returned to the dye cell until the light passes through one of the optic systems as a noncoherent laser beam. A tunable intracavity element tunes the laser across the gain curve of the dye solution. The pulse duration of the laser beam can be selected from a range of durations up to about one millisecond.

9 Claims, 2 Drawing Sheets

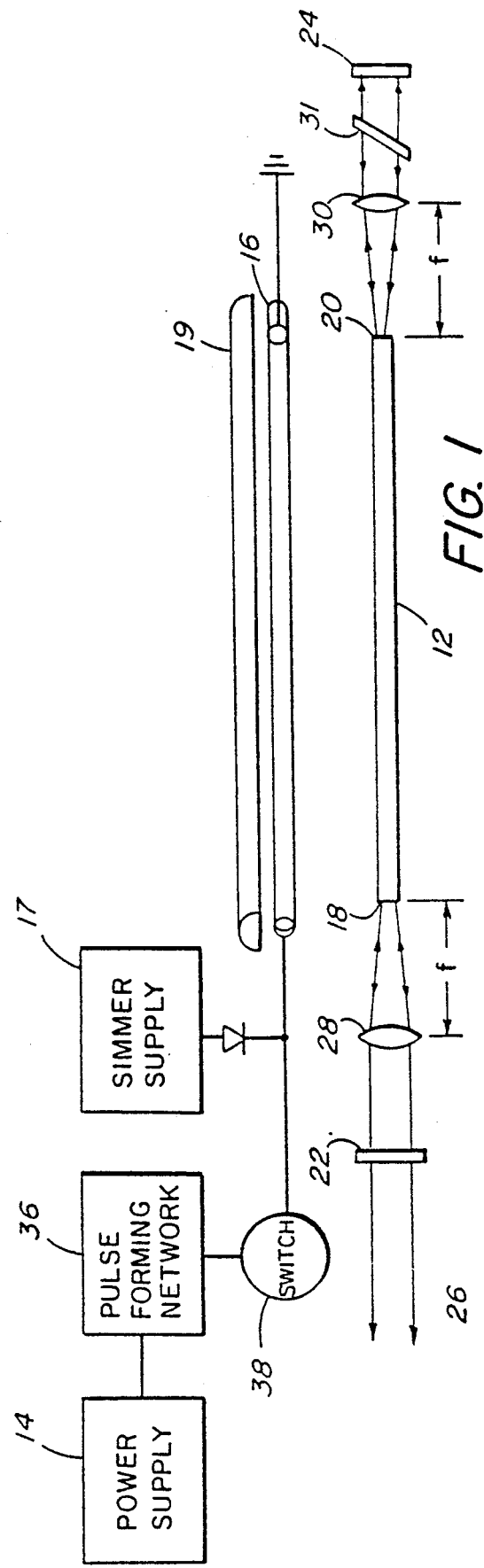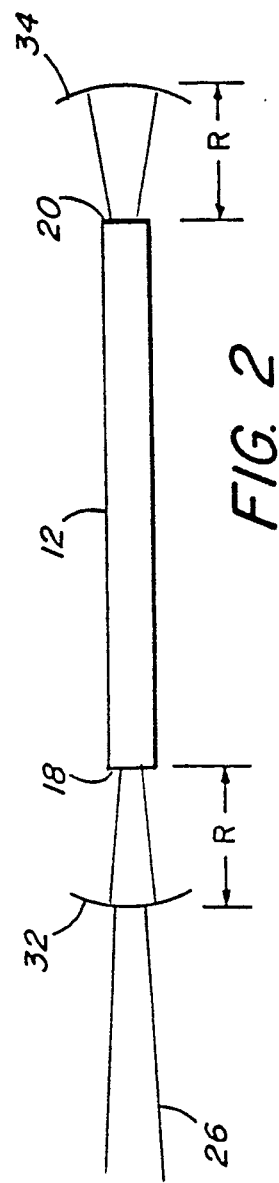

20µ SEC

20µSEC

LIGHT AMPLIFIER AND METHOD OF PHOTOTHEMOLYSIS

This application is a continuation of application Ser. No. 06/939,262, filed 12/8/86 now U.S. Pat. No. 4,824,262 which is a file wrapper continuing application of application Ser. No. 06/664,525 filed on Oct. 25, 1984, abandoned.

DESCRIPTION

1. Field of the Invention

This invention relates to lasers and in particular to laser systems suitable for medical applications such as selective photothermolysis.

2. Background

The use of lasers in selective photothermolysis has been reported by Greenwald et al., "Comparative Hystological Studies of the Tunable Dye (at 577 nm) Laser and Argon Laser: The Specific Vascular Effects of the Dye Laser", *The Journal of Investigative Dermatology* 77:305-310, 1981, and by Anderson and Parrish, "Selective Photothermolysis: Precise Microsurgery by Selective Absorption of Pulse Radiation", *Science* 220:524-527, 1983. In this technique, targeted tissues are heated by laser light, the wave length of which is selected to be specifically absorbed by the targeted tissues. The laser pulse duration is tailored to the size of the target. Tissues surrounding the targeted structures are spared.

The above studies highlight the need for selecting lasers which meet both the spectral requirements of a given application and pulse duration requirements. It is important that the laser be tunable to select the color of the source to match some spectral property of the targeted tissue. The special spectral features of targets require specific wavelengths, but only require moderate linewidths (1-4 nm) to induce selective effects. Proper laser pulse duration is important to heat target tissue to denature the tissues without boiling or vaporization. The temperature limits are tight, from body temperature of 35 C. to a temperature well below boiling point, about 70 C. Ordinary calorimetry states that temperature rise is proportional to energy and inversely proportional to target volume irrespective of the time it takes to deliver the energy. If thermal diffusivity is added there is a pulse duration criterion and the energy must be deposited quickly to minimize heat dissipation to surrounding tissue. However, selective photothermolysis heat must not be deposited too quickly so as to exceed the boiling point in the targeted zone.

The situation gets more complex if small absorbing chromophores such as hemoglobin in blood cells are used as absorbers to treat blood vessels which are an order of magnitude larger. The radiation must be added at low intensities so as not to vaporize the small cells, left on long enough to heat the blood vessels by thermal diffusion to the point of denaturation and then turned off before the surrounding tissue is damaged.

Some control in intensity is available by the adjustment of the spot size of the pulsed radiation source. A source capable of delivering more than a joule is necessary so that spot sizes do not become too tiny with a concomittant increase in treatment time.

The above studies have shown the dye laser to be particularly suited to selective photothermolysis. Dye lasers are readily tunable to selected wave lengths by means of the choice of dye, wavelength selective filters in the cavity and the like. Further, dye lasers can provide high output energies and short pulse durations. Unfortunately, the typical dye laser pulse duration of only a few microseconds or less is too short for many applications using selective photothermolysis. Dye lasers with nanosecond or shorter pulses are preferred for subcellular organelle targeting and microsecond or shorter pulses are preferred for cell targeting. However, dye lasers do not typically provide the millisecond pulses which are best for blood vessels and other small structures.

It is generally recognized that the quenching of a dye laser after microseconds may be due to the accumulation of dye molecules in the triplet state by means of intersystem crossing from the singlet state. Laser action in a dye laser starts from the singlet states. Molecules which cross over to the triplet state often absorb at the laser wavelength and inhibit laser action. The triplet state effect has been investigated and triplet state quenchers have been reported for specific dyes. However, triplet quenchers for all dyes used in lasers have not been identified. But, even with the use of triplet quenchers, pulse durations of several hundred microseconds have only been obtained at low energy outputs of not more than a few tenths of a joule.

A second problem that makes it difficult to generate long pulses in a dye laser is the distortion of the liquid amplifying medium by absorbed, conducted and convected heat from the laser excitation source. Such distortions are unavoidable but must be minimized for laser action to continue for milliseconds.

DISCLOSURE OF THE INVENTION

A laser has been developed which is more suitable for selective photothermolysis because the laser pulse duration is adjustable to durations approaching one millisecond. The present laser is based on the recognition that thermal distortion in the laser medium results in changes in the index of refraction in the medium and loss of resonating modes for which the laser is designed.

In accordance with principles of the invention, a multiple pass light amplifier, which may be considered a spatially noncoherent laser, comprises a cell having a medium excitable to an energy level with net optical gain and having apertures at opposite ends of the cell. The Fresnel number of the cell is greater than one, distinguishing it from wave guide lasers. Means such as a flashlamp is provided for raising the medium to an inverted energy configuration. An optical system at each end of the cell images each aperture upon itself. As a result, substantially all light emanating from the aperture, within a wavelength band determined by the dye solution and any tuning element, is returned to the cell through the aperture. The optical system at one end of the cell allows part of the light to escape and be used.

The resultant beam of light which passes through one of the optical systems has directional concentration to a solid angle substantially less than one steradian, in the order of $10^{-4}$ steradian, although that concentration is somewhat less than the solid angle of $10^{-8}$ steradian of conventional lasers. A pulse length greater than 100 microseconds, even approaching one millisecond, is possible even with output powers of over one tenth joule. In fact, a pulse duration of 500 microseconds has been obtained with output powers in the order of joules.

In one form of the embodiment, the means for imaging the aperture on itself is a spherical mirror located a distance from the aperture about equal to its radius of curvature. In another embodiment, a lens is positioned between the aperture and the flat mirror. The lens is positioned at about its focal length from the aperture. The light emanating from the cell is collected by the optical system and reflected back into the cell. The light traverses the cell in a number of total internal reflections off other cell walls. The dye solution in an excited state amplifies the light rays traversing the cell. The gain medium has a continually changing index of refraction, light rays traversing the cell have no fixed pattern and resonator modes are not established; rather, the spontaneous emission localized in a cone determined by the reimaging optics is amplified on successive round trips through the cell throughout the duration of the laser pulse.

In a system designed specifically for selective photothermolysis, the power supplied to the flashlamp is provided with a variable pulse length circuit which provides for variable length pulses in the range of at least about 10 to 500 microseconds. Preferably, the system allows for pulses of up to one millisecond duration. An output of at least about one joule is provided.

DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed on illustrating the principles of the invention.

FIG. 1 is an illustration of a preferred embodiment of the invention.

FIG. 2 is an illustration of an alternative embodiment of the invention using spherical mirrors.

DESCRIPTION OF PREFERRED EMBODIMENTS

Figure 3:
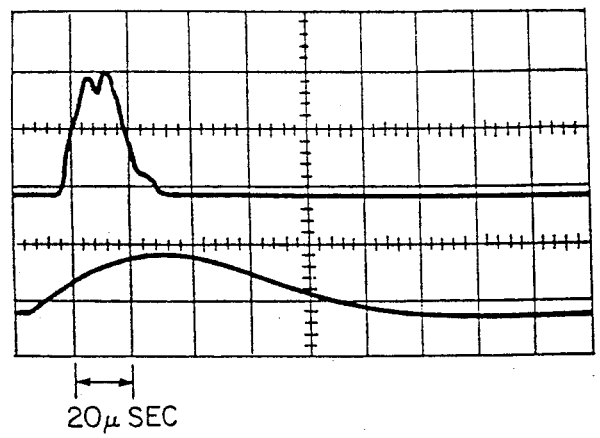
FIG. 3 graphically illustrates a typical laser pulse plotted over the flashlamp excitation pulse and showing thermal distortion in the laser pulse.

The earliest work in generating long pulses with dye laser concentrated on reducing triplet absorption effects. Dissolved oxygen and other chemicals considered to be triplet quenchers were added to the dye solution to deactivate any triplet states generated by long excitation pulses. Our present studies show that the additives or triplet quenchers do help to increase pulse duration. However, the additives may also help increase pulse duration because they lower laser threshold levels rather than minimize triplet absorption.

The early termination of laser action during a long excitation pulse is considered to be primarily of thermal origin. Heat is absorbed by the solution and heat is convected from the lamp to the dye cell if the pulse is long enough. Acoustic velocities are in the order of 0.5 mm/microsecond, and with a dye cell bore of 4 or 5 mm there will be density and index of refraction gradients throughout the cell when laser pulses are longer than ten microseconds. If the gradients are very large, the result is a loss of identifiable resonating modes and quenching of the laser output.

A laser system embodying the present invention is shown in FIG. 1. The system is a modification of a conventional flashlamp excited dye laser. In such lasers, a laser medium in the form of a dye carried by a liquid is directed through the dye cell from one end to the other. Through external temperature control equipment, the medium is maintained at a uniform and constant temperature. To excite the laser medium, a high voltage developed in a power supply 14 is applied across a flashlamp 16. As in conventional flashlamp excited dye lasers, a small simmering current may be applied from a supply 17 to the flashlamp prior to starting a pulse from the supply 14 in order to develop a significant level of ionization in the flashlamp prior to discharge.

Light energy from the flashlamp is directed inward to the laser medium by means of a reflector 19. The energy from the flashlamp is absorbed by the laser medium and moves molecules in the medium from the ground state to excited singlet states. As in conventional lasers, as those molecules return to their ground state they emit photons of a particular wavelength. Part of the light emanates from apertures 18 and 20 at each end of the dye cell. The light is returned through the apertures into the cell by respective mirrors 22 and 24. The returned photons react with molecules of the laser medium in the excited singlet state to cause those molecules to return to the ground state and themselves emit photons of the particular frequency. The thus emitted photons are in phase with the photons striking the molecules and are directed in the same direction as the original photons.

In a conventional laser, the optics at each end of the dye cell 12 are designed such that the photons travelling back and forth between the two mirrors 22 and 24 follow specific paths such that the photons resonate in particular modes. The photons resonate at a common frequency and phase. Finally, the light between the mirrors reaches an intensity such that a measurable amount passes through the mirror 22, which is not a full reflector, as a beam 26. In a conventional laser, the beam 26 is coherent and the divergence of that beam is very small, in the order of $10^{-8}$ steradians. To provide the resonating modes of a conventional laser, the laser optics must be precisely designed. Thermal distortions in the laser medium result in gradients in the index of refraction of the medium which in turn destroy the precise optic specifications of the system. The result is a loss of resonating modes and quenching of the laser output.

In the system of FIG. 1, lenses 28 and 30 are provided between respective apertures 18, 20 and mirrors 22, 24. In accordance with the present invention, the optics at each end of the dye cell are designed to return substantially all of the light emanating from the apertures 18 and 20 back into the dye cell rather than to return just the spatially coherent light which travels substantially coaxially in the system. There is no attempt to establish resonating and coherent modes in the present system.

The lenses 28 and 30 are positioned at about their focal lengths f from the apertures 18 and 20. As a result, each aperture is reimaged onto itself through the lenses and flat mirrors. By thus selecting and positioning the lenses, substantially all of the light emanating from the apertures, independent of resonating modes, is returned to the dye cell.

The optics mix the resonating rays and thoroughly homogenize the beams. Any thermal distortions which are induced by the flashlamp are of little consequence because there are no resonator modes. The rays traverse the cell and are amplified but do not follow a precise path determined by the optics. Those rays that are highly deviated as to miss the dye cell are lost. The homogenization is random and there is no phase relation at the wave front. The modes if any are randomly oriented and completely homogenized. The randomness is spatial as well as temporal. Spatial coherence is not preserved but monochromaticity can be partially preserved with suitable wavelength selective elements. The medium has gain and a definite threshold and therefore is classified a laser.

As in conventional lasers, a tuning element 31 may be provided to tune the laser output within the gain curve of the dye solution. The tuning element can reduce the bandwidth of the beam to less than 0.01 nanometers and is used to match the absorption band of the target to enhance the desired physiological effects. The most effective tuning elements are those that do not depend on this spatial coherence. The tuning element may be an etalon, a birefringent filter or a prism.

FIG. 2 illustrates an alternative embodiment of the invention in which the optics at each end of the dye cell are replaced with spherical mirrors 32 and 34. Each mirror is positioned at a distance from the aperture 18, 20 which about equals its radius of curvature R. Each spherical mirror reimages the aperture back on itself as do the optical systems in the prior embodiment.

The systems of FIGS. 1 and 2 do not provide the coherent radiation of a conventional laser, and their output beams diverge across a solid angle of $10^{-4}$ steradians. However, in an application such as selective photothermolysis, the large depth of field obtained from coherent radiation is not required. The concentration of light, though not as great as with the conventional laser, is significantly greater than the one steradian obtainable with nonlaser radiation and is adequate for selective photothermolysis. The advantage of the present system, as applied to selective photothermolysis, is that the beam is not limited by thermal distortion to a pulse duration of less than ten microseconds. Rather, pulse durations approaching one millisecond are possible.

There is a relation between laser pulse duration and the aspect ratio l/d where l is the cell length and d is the bore. A 12" gain length with a 4 mm bore cell lases for 125 microseconds before beam break up occurs. An 18" gain length laser with a 4 mm bore using the same set of optics lases for over 400 microseconds. The larger aspect ratio a/l where a is the radius of the dye cell bore and l the length of the cell, the longer are the pulses. The pumping intensities are kept constant by controlling the current density through the flashlamp. Energy levels up to five joules have been measured.

With the longer pulse durations available with the present system, the dye cell is now suited to a wider range of applications. Further, the pulse duration can be made variable to meet a number of different applications. To that end, a pulse forming network 36 is provided to generate electrical pulses and transmit the pulses to the flashlamp 16, through a relay switch 38. The pulse width may be selected from the range of 10 microseconds to 500 microseconds and preferably to as high as one millisecond.

Figure 4:
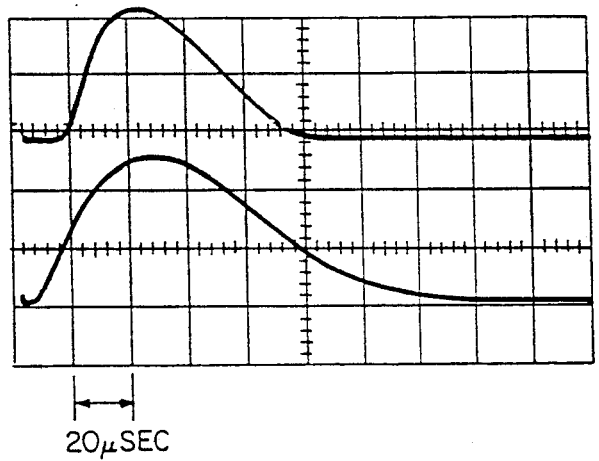
FIG. 4 is a graphical illustration of a laser pulse over the flashlamp excitation pulse in a system embodying the present invention.

Standard plane-plane or confocal laser resonators show thermal effects at times in the order of ten microseconds. The symptom for thermal distortion is an instability in the amplitude of the laser output pulse. In general, flashlamp excitation pulses have a smooth envelope and the laser output pulse closely follows the excitation pulse. If thermal effects distort the laser medium, then the laser intensity will show an amplitude fluctuation. FIG. 3 shows the output of a laser with a standard laser configuration; the laser pulse shows amplitude fluctuations after ten microseconds. Such amplitude fluctuations are seen in all long pulse dye lasers that use standard laser resonators. FIG. 4 shows the same laser with a laser resonator configuration according to this invention that compensates for the thermal effects; the amplitude fluctuations are eliminated.

This system is similar to a waveguide resonator in that the sum of the focal lengths is less than 1, the optical length between the mirrors. However, it is not a waveguide resonator for the following reasons. (1) There is no restriction on the Fresnel number of the guide. The Fresnel number is equal to $a^2/\lambda l$ where a is the radius of the dye cell, $\lambda$ is the wavelength, and l is the length of the cell. The waveguide resonator works with guides that have a Fresnel number less than one. Typical Fresnel number for the long pulse dye laser is 6 to 10 or even larger. For example, for a typical system a equals 2 mm, l equals 0.5 to 0.5 meters and $\lambda$ equals 0.5 micrometers. (2) The waveguide laser has resonator optics that match the free space $TEM_{oo}$ mode to some of the lower order waveguide modes such as the $HE_{01}$ or $HE_{11}$ mode. There is no such restriction in the present system. There is no unique curvature for the mirrors to go with the aperture of the waveguide as in the true waveguide laser. (3) Resonating modes are absent in the present sytem, and any ray that is reimaged on the exit/entrance aperture can have net gain. The beam divergence is large but still less than that emanating from a guide with a given numerical aperture, or from a tube whose optical beam divergence is defined by the aspect ratio of the tube. Because of the large beam divergence, tuning elements that depend on minimum beam divergence are not effective as line narrowing elements. However, etalons are effective and linewidths to 0.03 Angstroms have been obtained using the present system. Birefringent filters have also been used to tune the present system.

The present laser advantageously satisfies the criteria for selective photothermolysis. A dye laser emitting at 575 nm with pulse durations up to 400 microseconds has been developed for the treatment of cutaneous vascular lesions such as birthmarks. Such birthmarks are caused by a high density of blood vessels close to the surface of the skin. These blood vessels can be eliminated by selective photothermolysis. The selective photothermolysis laser should emit at 575 nm where blood has secondary absorption maxima at least an order of magnitude larger than that of pigmented tissue of fair skin. The laser should emit pulses about one millisecond long to couple energy into the blood vessels which are several hundred microns in diameter. The vessel will then be heated to denaturation temperature without vaporizing the blood cells. The laser should then be turned off before tissue surrounding the blood vessels is damaged.

A laser with variable pulse duration can be used in selective photothermolysis for a number of medical treatments other than the treatment of cutaneous vascular lesions. These include hemostasis of bleeding ulcers, suppression of choroidal neovascularization that leads to blindness, and hemostasis after the removal of eschar in burn therapy. If exogenous chromophores can be selectively injected into target tissue, the principle of selective photothermolysis treatment with tunable, variable pulse duration lasers can be extended to cover many medical applications too numerous to mention.

Figure 5:
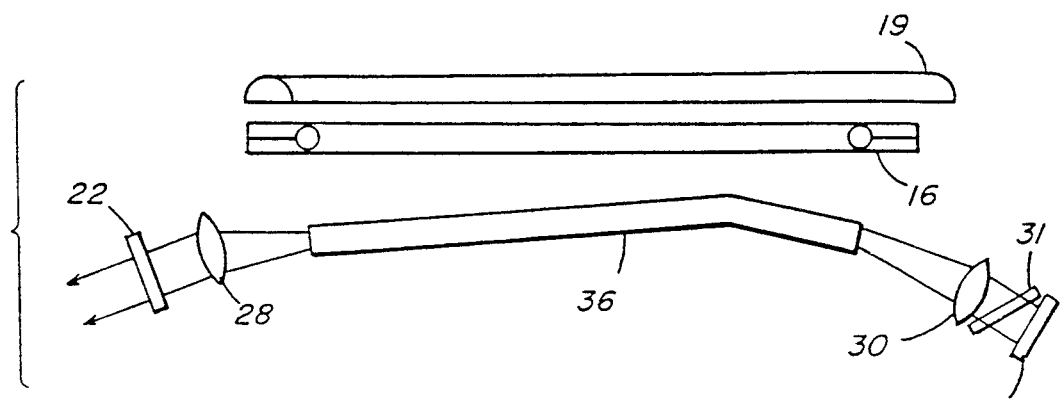
FIG. 5 is yet another embodiment of the invention having a bent gain medium.

FIG. 5 illustrates a modification of the system of FIG. 1 which is possible with the present system. Because the primary parameter of importance is the relation between the focal length of the optical system and the distance to the dye cell aperture and not the length of the dye cell itself, a bend as shown in the dye cell 36 of FIG. 5 is possible. With a conventional laser, that bend would provide different path lengths through the medium which would destroy the resonating modes of the system.

While the invention has been particularly shown and described with reference to preferred embodiments thereof, it will be understood by those skilled in the art that various changes in form and details may be made therein without departing from the spirit and scope of the invention as defined by the appended claims.

I claim:

1. A method of phothermolysis of biological tissue comprising:
    energizing a liquid dye medium in a dye cell including an aperture at each end thereof to an energy level at which the medium has net optical gain thereby producing an output beam from said dye cell;
    from each end of the cell returning into the cell substantially all light other than the output beam, within a wavelength band emanating from the cell, such that the light traverses the cell with internal reflections off cell walls and the cell amplifies the light, the light being returned including other than spatially coherent light traveling coaxially in the cell, the output beam being of at least one hundred microsecond duration and at least one-tenth joule; and
    illuminating the biological tissue with the output beam from the cell.

2. A method as claimed in claim 1 including the step of amplifying the light to form a beam of light which is spatially noncoherent and has a directional concentration to a solid angle of about $10^{-4}$ steradian or less.

3. A method as claimed in claim 1 further comprising the step of reducing the bandwidth of the output beam by means of a tuning element.

4. A method as claimed in claim 1 wherein the step of collecting light includes returning the light to at least one end of the cell by a mirror spaced from the cell.

5. A photothermolysis method of treating cutaneous vascular lesions comprising:
    energizing a liquid dye medium in a dye cell including an aperture at each end thereof to an energy level at which the medium has net optical guide thereby producing an output beam from said dye cell;
    from each end of the cell returning into the cell substantially all light other than the output beam, within a wavelength band emanating from the cell, such that the light traverses the cell with internal reflections off cell walls and the cell amplifies the light, the light being returned including other than spatially coherent light traveling coaxilly in the cell, the output beam being of at least one hundred microsecond duration and at least one-tenth joule; and
    illuminating the lesions with the output beam from the cell.

6. A method as claimed in claim 5 including the step of amplifying the light to form a beam of light which is spatially noncoherent and has a directional concentration to a solid angle of about $10^{-4}$ steradian or less.

7. A method as claimed in claim 5 further comprising the step of reducing the bandwidth of the output beam by means of a tuning element.

8. A method as claimed in claim 5 wherein the step of collecting light includes returning the light to at least one end of the cell by a mirror spaced from the cell.

9. A multiple pass light amplifier comprising;
    a cell having a medium excitable to an energy level with net optical gain and apertures at opposite ends thereof, a Fresnel number of the cell being significantly greater than one, the cell being bent along the optic axis between the apertures;
    means for raising the energy level of the medium to have net optical gain; and
    an optical system at each end of the cell including means for returning light from the cell into the cell such that the light traverses the cell with internal reflections off cell walls and the cell amplifies the light to form a spatially noncoherent beam of light, the light being returned including other than spatially coherent light traveling coaxially in the cell.

* * * * *